Figure 1:
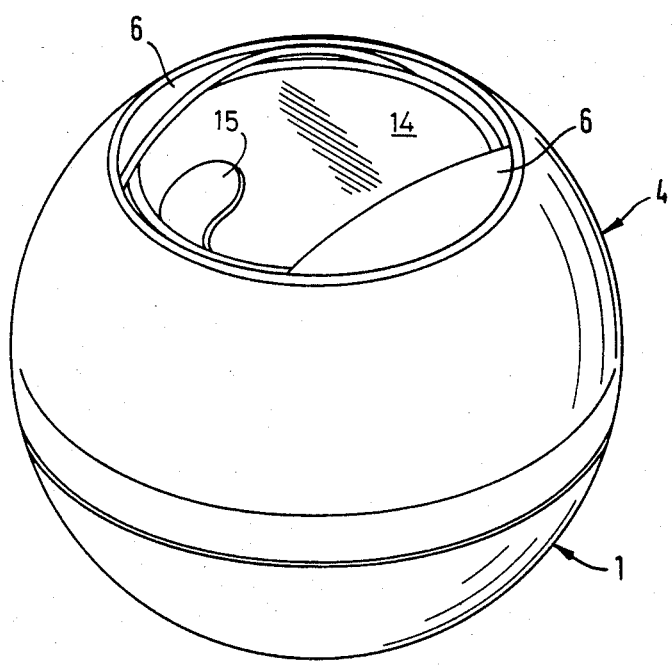

United States Patent [19]

Joyaux et al.

[11] Patent Number: 4,660,764
[45] Date of Patent: Apr. 28, 1987

[54] DEVICE FOR PERMITTING CONTROLLED EMISSION OF VOLATILE SUBSTANCES

[75] Inventors: Yves Joyaux, Vouille; Jean-Pierre Mandon, Montamise Tronc, both of France

[73] Assignee: Reckitt and Colman AG, Basel, Switzerland

[21] Appl. No.: 853,779

[22] Filed: Apr. 18, 1986

[30] Foreign Application Priority Data

Apr. 26, 1985 [CH] Switzerland ............... 01777/85

[51] Int. Cl.⁴ ............................................. A24F 25/00
[52] U.S. Cl. ........................................ 239/44; 239/47; 251/212
[58] Field of Search ............... 251/212; 239/44, 47, 239/50; 98/105, 109

[56] References Cited

U.S. PATENT DOCUMENTS

| | | | |
|---|---|---|---|
| 214,394 | 4/1879 | Ball | 239/47 |
| 2,508,615 | 5/1950 | Lukes | 251/212 |
| 2,513,272 | 7/1950 | Bowen | 251/212 |
| 2,898,080 | 8/1959 | Smith | 251/212 |
| 3,727,840 | 4/1973 | Nigro | 239/47 |
| 4,274,437 | 6/1981 | Watts | 251/212 |
| 4,293,095 | 10/1981 | Hamilton et al. | 239/47 |
| 4,323,193 | 4/1982 | Compton et al. | 239/44 |

Primary Examiner—Henry C. Yuen
Attorney, Agent, or Firm—Frederick H. Rabin

[57] ABSTRACT

A device for permitting controlled emission of a volatile substance, in particular an air-treating agent. The device comprises a container having an annular ledge with two recesses on opposite sides and a frustro hemispherical hood open at the top, that fits on to the container. The hood has two studs protruding on opposite sides of its inner wall. Inside the hood are situated two shutters that are moveable in relation to each other on relative rotation between the container and the hood by means of slots, which are moved by the studs, to close or open the opening to an infinitely variable degree.

5 Claims, 6 Drawing Figures

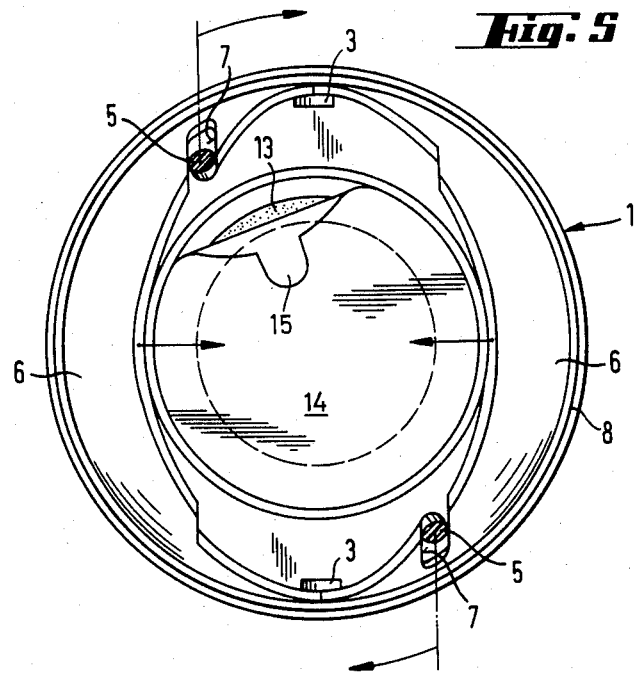
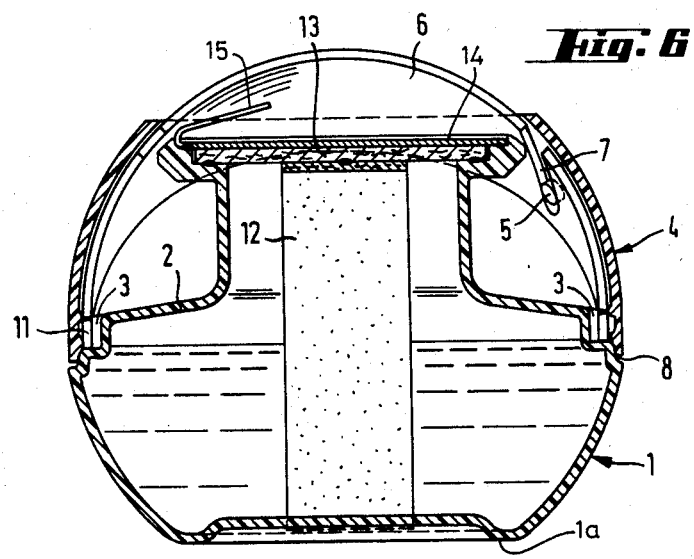

DEVICE FOR PERMITTING CONTROLLED EMISSION OF VOLATILE SUBSTANCES

The present invention relates to a device for permitting controlled emission of a volatile substance from fluid in a container.

Devices for permitting emission of a volatile substance commonly incorporate a wick immersed in fluid, with the upper portion of the wick exposed to atmosphere; the amount so exposed governing the amount of continuous emission. Most emission devices are equipped with a fixed of adjustable wick and/or adjustable aperture.

Emitters with a fixed wick have the disadvantage that they cannot be regulated (GB-A No. 2 006 012), while those with an adjustable wick are complicated to operate and tend to get dirty (U.S. Pat. Nos. 2 826 452 and 3 028 100). In emission devices with adjustable aperatures (EP-A No. 28 852) the evaporation surface is too great for the apertures, so that they take up more room. Another disadvantage is that their manufacture by the usual injection moulding methods presents problems, because the tools required are fairly complicated and the parts of the devices themselves difficult to mould, so that there is a risk of imperfections that affect adjustment of the device.

An object of the present invention is to reduce and possibly avoid these disadvantages. It is also an object of the present invention to provide total availability of an evaporation surface, simplicity of manufacture by for example injecting moulding, simple mode of operation and ease of use.

According to the present invention there is provided a device for permitting controlled emission of a volatile substance from a fluid in a container; characterised by a container (1) which has an annular ledge (2) provided with recesses (3) at opposite sides of its circumference, a frustro-dome shaped hood (4) located on the container (1), which hood (4) has two studs (5) on opposite sides of its inner wall, and emission control means within the hood (4), which emission control means comprise two shutters (6) moveable with respect to each other and having slots (7) in which the studs (5) are located wherein on rotation of the hood (4) relative to the container (1) the studs (5) move at an angle to the center lines of the slots (7) to cause the shutters to vary the size of the opening in the hood.

The container may comprise a circumferential step below the ledge on which step the hood rests.

The step may be provided with a circumferential groove and the inner wall of the hood may be provided with protrusion means which engage in the groove.

The shutters may be intergrally hinged and location means may be provided where the shutters are hinged, which location means locate in the recesses of the container.

One or more wicks may extend downwardly into the interior of the container, which wicks communicate with a circular evaportion surface at an upper region of the container.

Figure 2:
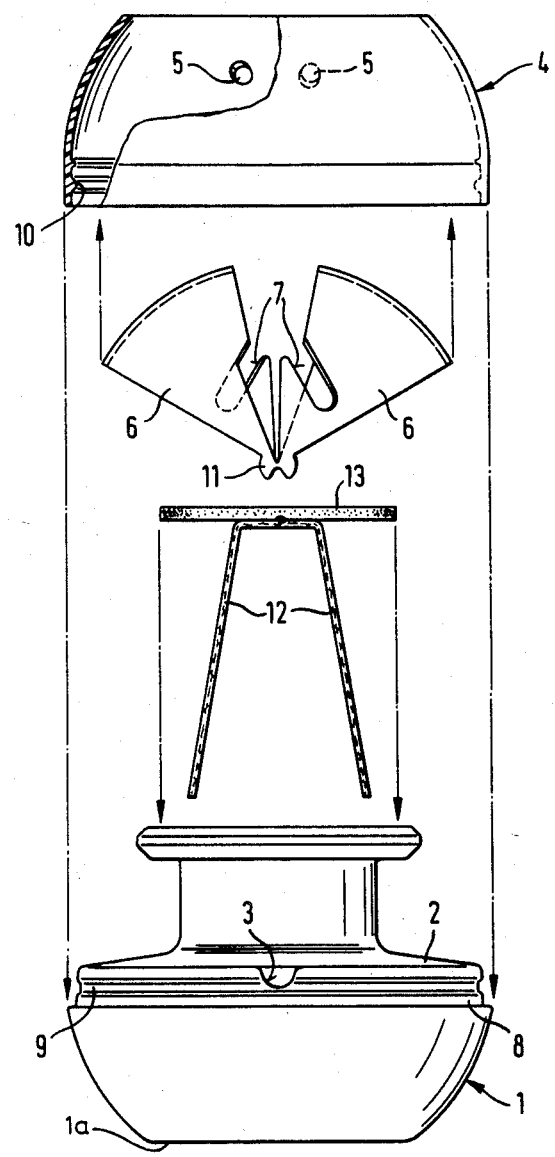
Figure 3:
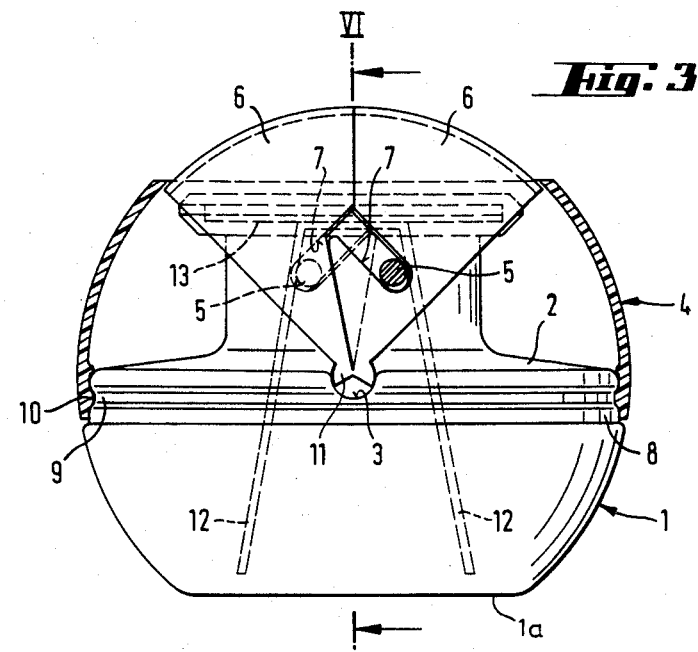
Figure 4:
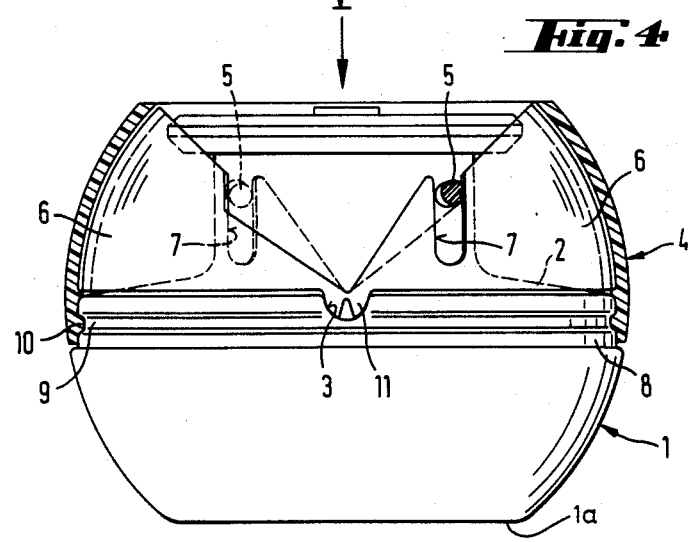

The present invention will now be described by way of example and with reference to the accompanying drawings in which:

FIG. 1 shows a perspective view of an embodiment of the device in which the shutters almost expose the opening in the hood, FIG. 2 shows an exploded sectional view of the device illustrated in FIG. 1, FIG. 3 shows a sectional view of the device in which the opening in the hood is closed by the shutters, FIG. 4 shows a sectional view of the device in which the opening in the hood is entirely exposed, FIG. 5 shows a plan view of FIG. 4 taken in the direction of arrow V, and FIG. 6 is a section taken along VI—VI of FIG. 3.

Referring to the drawings, there is shown a device for permitting controlled emission of a volatile substance, comprising a container having a frustro hemispherical wall and a slightly recessed base 1a. The upper region of the frustro hemispherical wall merges into a circumferential groove 9 which has a circumferential step 8 between the upper region of the wall and the groove 9.

Above the groove 9 the container 1 comprises an annular ledge 2 which tapers upwardly to a neck and then diverges to an upper surface. Located in the container at the upper surface is a circular evaporation surface 13 which is connected to two spaced wicks 12 depending into fluid in the container 1.

Covering the surface 13 is a foil 14 (FIG. 1) which is provided with a tag 15.

Located on the container 1 is a frustro hemispherical hood 4 which has a plurality of protrusions 10 around its circumference. These protrusions 10 locate in the groove 9 in the container and permit the hood 4 to be rotated relative to the container 1. A respective recess 3 is situated at diametrically opposite sides of the groove 9. Within the hood 4 are disposed two shutters 6 which are integrally hinged to each other at their lower ends where they are provided with two location means 11 which each locate in a respective one of the recesses 3.

The shutters are each provided with a slot 7 in which locate a respective one of two studs 5 protruding from opposite sides of the hood 4.

By rotating the hood 4 in one direction with respect to the container 1 on the groove 9 the studs 5 act on the slots 7 to cause the shutters to spread out to expose a greater part of the opening in the hood 14, and by rotation of the hood in the opposite direction a lesser part of the opening is exposed so that at the extreme extents of rotation the opening in the hood 4 is either completely exposed or completely closed. In order to facilitate the opening and closing of the shutters 6 they are hinged at their lower end and provided at the hinged region with location means 11 which locate in recesses 3 in the container 1. The shutters 6 are intergral with each other and the hinge is formed from a thin portion of the shutters 6. The location means 11 is in the form of wing like elements which locate in the recesses 3 on the container.

The base 1a of the container 1 can be of any desired shape, and from the base to the ledge 2 it may be cylindrical, conical or spheroidal, to permit its transformation into the annular ledge 2. Preferably the lower part of the container 1 is in the form of a round bowl, tapering towards a flat bottom. The fluid in the container can be volatilised to act as an insecticide, germicide or deodoriser.

The fluid is drawn up the wicks 12 to the evaporation surface 13. Only this surface 13 is visible and exposed to the air when the device is in the open position. The device is designed to provide the emission of a controllable amount of a fluid agent located in a container, so one of its purposes is spatial distribution of an air-conditioning agent. However, it can be used for the emission of other volatile agents such as insecticides and germicides.

The device is perferably made from plastic material, in particular from plastics material that can be injection-moulded, such as polyethylene or PVC. However, the container may be made of some other material, e.g. glass or porcelain.

We claim:

1. A device for permitting controlled emission of a volatile substance from a fluid, which device comprises:
    a container adapted to hold a volatile liquid and having an annular ledge provided with recesses at opposite sides of the ledge,
    a circular evaporation surface in an upper region of the container,
    one or more wicks extending downwardly from the circular evaporation surface into the interior of the container,
    a frustro-dome shaped hood mounted on the container, said hood having two studs on opposite sides of its inner wall, and
    emission control means within the hood, said means comprising two shutters movable with respect to each other and having slots in which the studs are located,
    whereby, on rotation of the hood relative to the container, the studs move at angle to the center lines of the slots, causing the shutters to vary the size of the opening in the hood.

2. A device as claimed in claim 1 in which the container is additionally provided with a circumferential step below the ledge on which step the hood rests.

3. A device as claimed in claim 2, in which the step is provided with a circumferential groove and the inner wall of the hood is provided with protrusion means which engage in the groove.

4. A device as claimed in any one of the preceding claims in which the shutters are integrally hinged.

5. A device as claimed in claim 4 in which location means are provided where the shutters are hinged, which location means locate in the recesses of the container.

* * * * *